US008223322B2

(12) United States Patent
Breugnot et al.

(10) Patent No.: US 8,223,322 B2
(45) Date of Patent: *Jul. 17, 2012

(54) VISUAL APPEARANCE MEASUREMENT METHOD AND SYSTEM FOR RANDOMLY AND REGULARLY ARRANGED BIREFRINGENT FIBERS

(75) Inventors: Sebastien Breugnot, Los Angeles, CA (US); Nicolas Lechocinski, Los Angeles, CA (US); Bruno Fraçois Pouet, Los Angeles, CA (US)

(73) Assignees: Bossa Nova Technologies, LLC, Venice, CA (US); The Procter & Gamble Company, Cincinnati, OH (US)

( * ) Notice: Subject to any disclaimer, the term of this patent is extended or adjusted under 35 U.S.C. 154(b) by 218 days.

This patent is subject to a terminal disclaimer.

(21) Appl. No.: 12/727,152

(22) Filed: Mar. 18, 2010

(65) Prior Publication Data

US 2011/0074946 A1    Mar. 31, 2011

Related U.S. Application Data

(63) Continuation-in-part of application No. 12/567,599, filed on Sep. 25, 2009.

(51) Int. Cl.
*G01N 21/00* (2006.01)
*G01J 4/00* (2006.01)
(52) U.S. Cl. .................................... 356/73.1; 356/364
(58) Field of Classification Search .................. None
See application file for complete search history.

(56) References Cited

U.S. PATENT DOCUMENTS

| 6,069,565 | A  | * | 5/2000 | Stern et al. .................. 340/583 |
| 6,097,488 | A  |   | 8/2000 | Grek et al. |
| 7,764,380 | B2 | * | 7/2010 | Van Hal et al. ............... 356/445 |
| 7,986,401 | B2 | * | 7/2011 | Lechocinski et al. ........ 356/73.1 |
| 2002/0057438 | A1 | * | 5/2002 | Decker ........................ 356/601 |
| 2003/0045799 | A1 |   | 3/2003 | Bazin et al. |
| 2003/0156293 | A1 | * | 8/2003 | Kazuhiko et al. ............. 356/446 |
| 2006/0255300 | A1 | * | 11/2006 | Shakespeare ............ 250/559.37 |

(Continued)

FOREIGN PATENT DOCUMENTS
EP    0 440 907    8/1991

OTHER PUBLICATIONS

Lechocinski, N. et al., 'Samba Hair System—Hair Visual Appearance Characterization-,' Mar. 2009, Bossa Nova Technologies, pp. 1-21.*

(Continued)

*Primary Examiner* — Tarifur Chowdhury
*Assistant Examiner* — Gordon Stock, Jr.
(74) *Attorney, Agent, or Firm* — Osha • Liang LLP

(57) ABSTRACT

A method for measuring visual appearance of birefringent fibers is disclosed. The method involves emitting light, creating N polarization states of the emitted light, wherein the polarized emitted light illuminates the birefringent fibers, thereby generating internal reflection components, external reflection components, and diffusion components of the light, observing the light from the illuminated birefringent fibers, creating N polarization states of the observed light, forming N images of the observed polarized light, each image comprising a plurality of pixels, measuring the intensity in each pixel of the N images, and for each pixel, separating the internal reflection component, the external reflection component, and the diffusion component from the i-th image for the N images, wherein i=1, 2, ... N and N≥4.

22 Claims, 6 Drawing Sheets

U.S. PATENT DOCUMENTS

| | | | |
|---|---|---|---|
| 2008/0147054 A1* | 6/2008 | Altshuler et al. | 606/9 |
| 2008/0259345 A1* | 10/2008 | Fukutake | 356/450 |
| 2010/0008588 A1* | 1/2010 | Feldkhun et al. | 382/206 |
| 2010/0063491 A1* | 3/2010 | Verhagen et al. | 606/9 |
| 2011/0134285 A1* | 6/2011 | Kanamori et al. | 348/240.3 |

OTHER PUBLICATIONS

Lefaudeux, N. et al., 'New luster formula for the characterization of hair tresses using polarization imaging,' Sep. 2008, Third Annual Conference on Applied Hair Science, pp. 1-16.*

Gao, Timothy et al., 'Study of hair shine and hair surface smoothness,' Mar./Apr. 2009, Journal of Cosmetic Science, 60, pp. 187-197.*

Combined Search and Examination Report from the UK Intellectual Property Office, dated May 27, 2010, for patent application No. GB1004927.8, 5 pages.

Office Action for U.S. Appl. No. 12/567,599 mailed Dec. 19, 2011 (12 pages).

Lechocinski, N. et al., "Samba Hair System—Hair Visual Appearance Characterization-", Bossa Nova Technologies, Mar. 2009 pp. 1-21.

Lefaudeux, N. et al., "New Luster Formula for the Characterization of Hair Tresses Using Polarization Imaging", Third Annual Conference on Applied Hair Science, Sep. 2008, pp. 1-16.

Gao, Timothy et al., "Study of Hair Shine and Hair Surface Smoothness", Journal of Cosmetic Science, Mar./Apr. 2009, 60, pp. 187-197.

* cited by examiner

VISUAL APPEARANCE MEASUREMENT METHOD AND SYSTEM FOR RANDOMLY AND REGULARLY ARRANGED BIREFRINGENT FIBERS

CROSS-REFERENCE TO RELATED APPLICATIONS

The present application claims benefit under 35 U.S.C. §120 as a continuation-in-part of U.S. patent application Ser. No. 12/567,599 and, accordingly incorporates the '599 application by reference in its entirety.

BACKGROUND

1. Field of the Disclosure

The present disclosure relates generally to an apparatus and a method for the measurement of the visual appearance of randomly and regularly (i.e., non-randomly) arranged birefringent fibers, such as for example textile fibers and hair.

2. Background Art

Polarization imaging is being used in many applications. In passive imaging, where the illumination is not controlled, i.e., not actively polarized, polarization imaging can be used, for example, to enhance the contrast between human made objects that have a strong polarization signature from the natural background. It also provides information on the shape of the objects. Further, polarization imaging conveniently allows for the detection of water or mud surfaces thanks to the strong polarization signature of water.

In active imaging, where the illumination is controlled and polarized, polarization imaging can be used to study light scattering. In fact, two-state polarization allows for easy separation of the surface scattering from the volume scattering. Specular reflections and color information, which determine the visual appearance of an object, can therefore be separated, thus providing information on the structure of the studied object.

Polarization imaging is applied, for example, in the cosmetic industry with the aim of studying the visual appearance (of the skin, the hair, etc.). Polarization imaging can be used as a tool to improve formulation for both hair and skin care products, such as styling products, for example by visualizing the improvement of the structure and appearance of hair once the product is applied.

The light reflected by birefringent fibers, such as human hair, contains components from the different interactions of the light with the fibers. The three components that may be observed are the following:

- light coming from the external reflection, i.e., light that is reflected on the external surface of the fiber. The externally reflected light has the same wavelength (color) as the incident light.
- light coming from the internal reflection on an internal surface of the fiber. Since this component propagates through the fiber, it experiences a change of wavelength.
- diffused light from volume scattering inside the fiber.

This general situation is depicted in FIG. 1 with a single fiber 3a. The visual appearance of the fibers is based on these three different contributions.

Currently, no system or method allows for physically separating these three components in randomly and regularly arranged birefringent fibers. A method is known for separating the specular reflection component, that contains information on the internal reflection (color) and external reflection (shine) components, from the diffused light using polarization imaging (in: Journal of Cosmetic Science, Bossa Nova Tech, 60, 153-169, March-April 2009) in regularly arranged fibers. Two images corresponding to two couples of polarization states are acquired, a couple of polarization states corresponding to the polarization of the illumination and the observation channel. Using an algorithm, the color and shine signals of the specular light are analyzed so as to separate the internal reflection component from the external reflection component as functions of the angle of incidence of the illuminating light. However, this method requires that the fibers all have the same orientation because information extraction per pixel is not possible. Further, this mathematical method necessitates making assumptions about the internal reflection.

Therefore, there is a need to provide an improved method and an improved apparatus for the visual appearance measurement of randomly and regularly arranged birefringent fibers by a physical decomposition of the measured light in each image pixel into the internally and externally reflected light and the diffusion components, without the necessity to make any assumptions.

SUMMARY OF THE CLAIMED SUBJECT MATTER

In a first aspect, the present disclosure relates to a method for the measurement of visual appearance of randomly and regularly arranged birefringent fibers. The method comprises emitting light, creating N polarization states of the emitted light, illuminating the birefringent fibers with the emitted light so polarized, thereby generating N internal reflection components, N external reflection components, and N diffusion components of the light in the birefringent fibers, observing the light from the illuminated birefringent fibers, creating N polarization states of the observed light, forming N images of the observed polarized light, each image comprising a plurality of pixels, measuring the intensity $I_i$ in each pixel of the N images, and for each pixel, separating the internal reflection component, the external reflection component, and the diffusion component from the i-th image for the N images, wherein i=1, 2, ..., N and $N \geq 4$.

Preferably, the birefringent fibers comprise one of textile fibers and hair.

Preferably, the wavelength of the emitted light is in the near infrared range.

According to an alternative preferred embodiment, the wavelength of the emitted light is in the visible range.

Preferably, at least one of the polarization states of the emitted light and at least one of the polarization states of the observed light are the same.

According to an alternative preferred embodiment, at least one of the polarization states of the emitted light is different from at least one of the polarization states of the observed light.

Preferably, the separating comprises analytically resolving for each pixel an equation system for the intensities measured in the N images.

In a second aspect, the present disclosure relates to an apparatus for the measurement of visual appearance of randomly and regularly arranged birefringent fibers. The apparatus comprises a light source for emitting light, a first variable polarizer for creating N polarization states of the emitted light, the polarized emitted light illuminates the birefringent fibers, thereby generating internal reflection components, external reflection components, and diffusion components of the light, a detector for observing the light from the illuminated birefringent fibers, a second variable polarizer for creating N polarization states of the observed light, wherein the detector is intended to form N images of the observed polarized light, each image comprising a plurality of pixels, and an image processing unit intended to measure the intensity in each pixel of the N images and for each pixel, to separate the internal reflection component, the external reflection component, and the diffusion component from the i-th image for the N images, wherein i=1, 2, . . . , N and N≧4.

The light source may, for example, comprise a pulsed laser source, a continuous wave (cw) laser source, at least one light emitting diode, or a flash lamp.

Preferably, the detector comprises a video camera.

Preferably, each one of the first and the second variable polarizers is actively controlled. However, passively controlled polarizers may also be used. Combinations of actively and passively controlled polarizers may also be envisaged.

Preferably, the first and the second variable polarizers are integrally formed. In other words, the first and the second variable polarizers may be incorporated in a single unit.

Preferably N first and second polarizers are mounted on one rotation stage.

Preferably, the image processing unit and the processor are incorporated in a computer.

Preferably, the apparatus further comprises a synchronization unit configured to synchronize the first and second variable polarizers and the detector.

Other aspects, characteristics, and advantages of the invention will be apparent from the following detailed description.

BRIEF DESCRIPTION OF THE DRAWINGS

FIG. 6a shows the total intensity, FIG. 6b shows the external reflection component, FIG. 6c shows the internal reflection component, and FIG. 6d shows the diffused light component.

DETAILED DESCRIPTION

Figure 1:
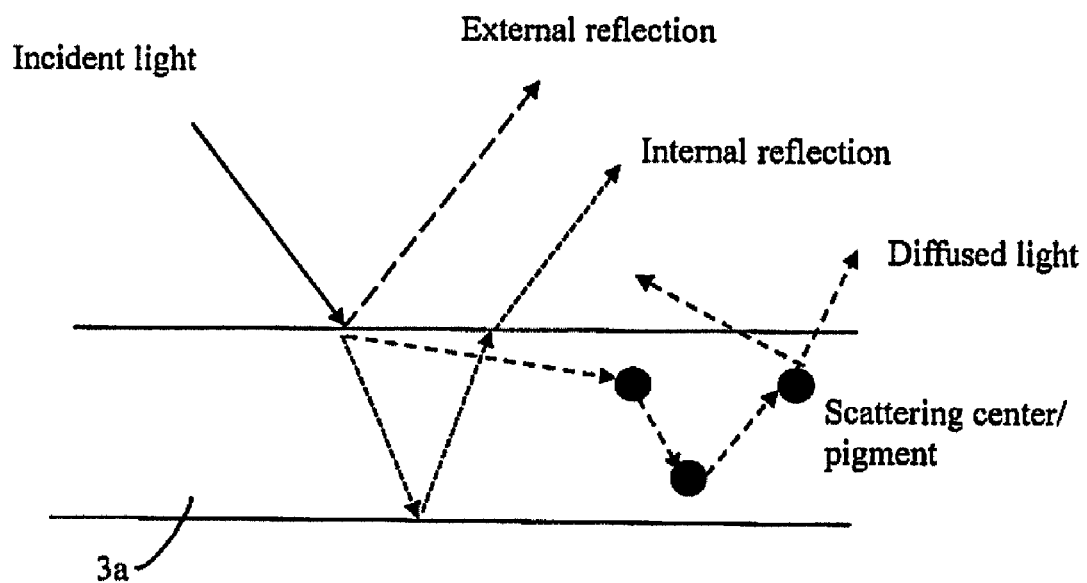
FIG. 1 shows a model of light interaction with a single translucent fiber.

Specific embodiments of the present disclosure will now be described in detail with reference to the accompanying Figures. Like elements in the various Figures are denoted by like reference numerals for consistency.

In general, embodiments of the present disclosure relate to apparatus and methods for measuring the visual appearance of randomly and regularly organized birefringent fibers. More specifically, embodiments of the present disclosure provide methods and apparatus for decomposing measured light from birefringent fibers into the internally and externally reflected light and the diffusion components.

We will describe preferred methods and apparatus for the visual appearance measurement of randomly and regularly organized birefringent fibers using a polarization analysis technique. This technique is based on the polarization signature carried by each of the external reflection, the internal reflection, and the diffusion components in birefringent fibers. The birefringent fibers may be, for example, human hair or textile fibers, such as for example Nylon fibers or any other birefringent translucent fibers.

Figure 2:
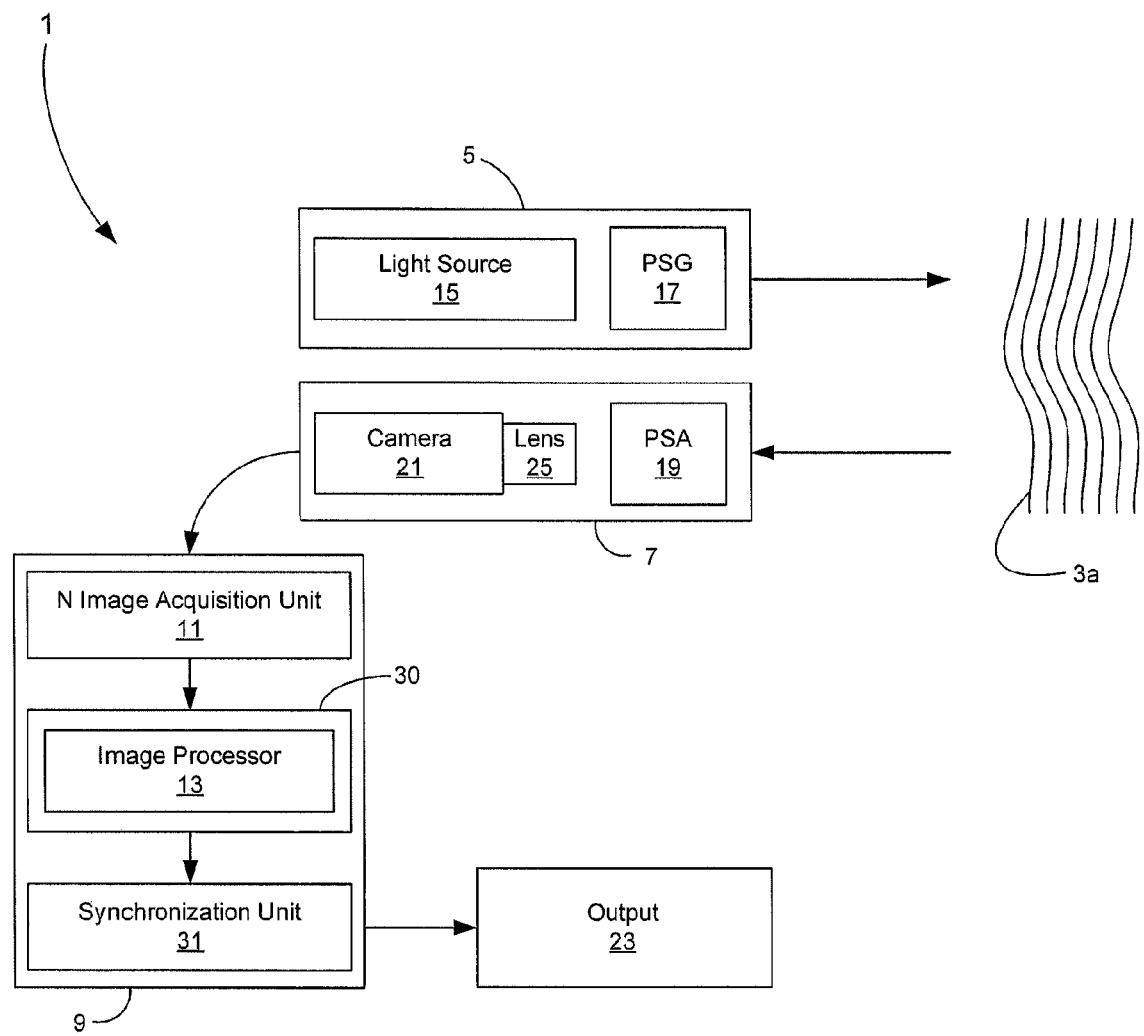
FIG. 2 schematically shows an apparatus for the visual appearance measurement of birefringent fibers according to a preferred embodiment of the present disclosure.

FIG. 2 schematically shows an apparatus 1 for the visual appearance measurement of birefringent fibers 3a according to a preferred embodiment of the present disclosure. The birefringent fibers 3a are randomly arranged, and no control of their organization is performed. The birefringent fibers 3a may also be regularly organized, or the birefringent fibers 3a may be a combination of randomly and regularly organized. The apparatus 1 comprises a light source 15, a polarization state generator (PSG) 17, a polarization state analyzer (PSA) 19, and a detector (shown as elements 21 and 25). The light source 15 and the polarization state generator (PSG) 17 may be parts of a polarization illumination system 5, and the polarization state analyzer (PSA) 19 and the detector may be parts of a polarization imaging system 7. The detector is preferably video camera 21. The video camera 21 preferably comprises an objective lens 25. The light source 15 may be a pulsed or a continuous wave (cw) laser source, one or a plurality of light emitting diodes (LED), a flash lamp, or any other light source known in the art. The wavelength of the light source 15 is preferably chosen according to the type of fibers that are to be measured, i.e., their color and/or their absorption coefficient. For example, for human hair, the wavelength preferably ranges from the visible spectrum to the near infra-red.

The apparatus 1 further comprises a control unit 9, such as a personal computer. The control unit 9 comprises an image acquisition unit 11, an image processing unit 13, and a processor 30. The image acquisition unit 11 may also be separate from the control unit 9. Further, the apparatus comprises an output device 23. The output device 23 may comprise, for example, a screen of a personal computer or a printer.

The PSG 17 and the PSA 19 preferably comprise a first and a second variable polarizer, respectively. The PSG 17 and the PSA 19 may comprise actively or passively controlled polarizing components. For example, they may comprise electronically controllable liquid crystals or conventional polarization components positioned on a rotation stage that is rotated mechanically.

Further, the apparatus 1 may comprise a black screen 27 that is adapted to eliminate any parasite reflection on the fibers 3a.

Figure 3:
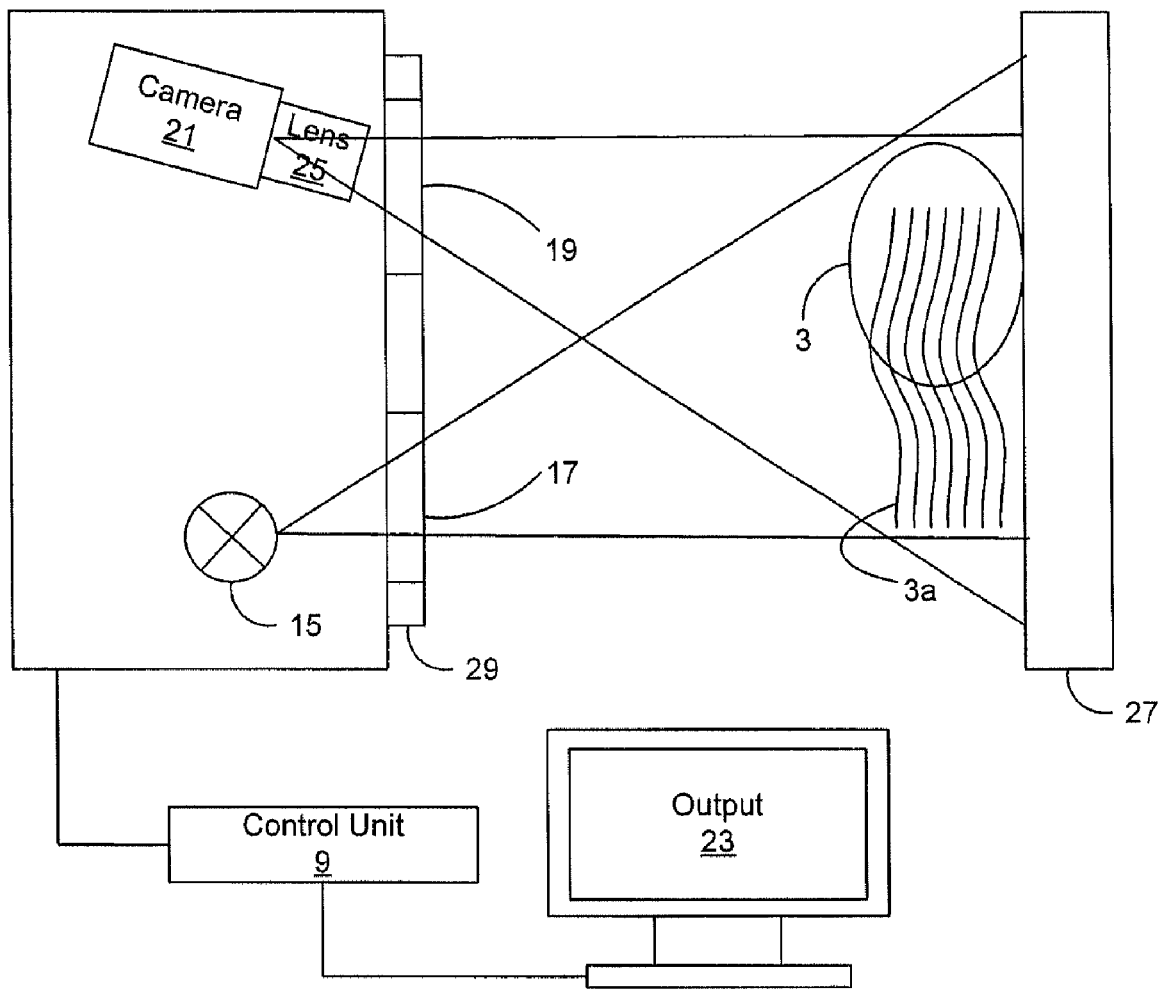
FIG. 3 shows a schematic view of a further preferred embodiment of an apparatus according to the present disclosure.

FIG. 3 shows an example setup of the visual appearance measurement apparatus 1 according to a preferred embodiment. Other configurations that are different from the one as shown are also possible, depending on user-specific requirements. The light source 15 consists of a matrix of white LEDs. However, any other light source may be used. A filter may be placed in front of the LED matrix to filter out NIR and UV light emitted by the LEDs. The polarization state of the emitted light is set by the PSG 17. The PSG 17 and the PSA 19 may be mounted together on a rotation stage 29. A mannequin head 3 with human hair as birefringent fibers 3a is illuminated by the polarized incident light.

Figure 3A:
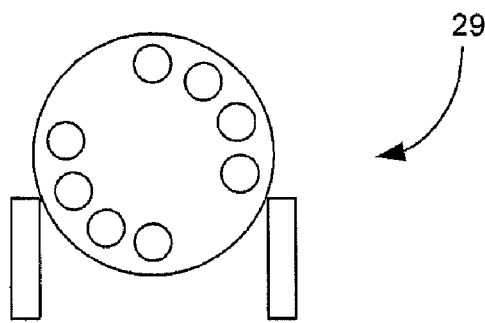
FIG. 3a shows an example of a rotation stage comprising a first and a second polarizer of the apparatus according to the present disclosure.

An example of a rotation stage 29 comprising 4 couples of PSG/PSA 17, 19 is shown in FIG. 3a. For each image acquisition, one couple of PSG/PSA may be chosen so as to position the PSG in front of the light source and the PSA in front of the camera. In this example, the polarizers are linear polarizers made of glass or film with high contrast ratio.

In the case of polarized incident light, the externally reflected light remains polarized with the same polarization, the internally reflected light becomes elliptically polarized, and the diffused light becomes depolarized.

If the incident light is polarized, two cases may be distinguished:
  i) the polarization state of the incident light is linear and parallel to a neutral axis of birefringence of the fibers, and
  ii) the polarization state of the incident light is such that there is the projections of the polarization components on the neutral axis and the axis perpendicular to it are equal. For example, the incident light may be circularly polarized or linearly polarized with an orientation at 45° with respect to the neutral axis of the fiber).

Figure 4A:
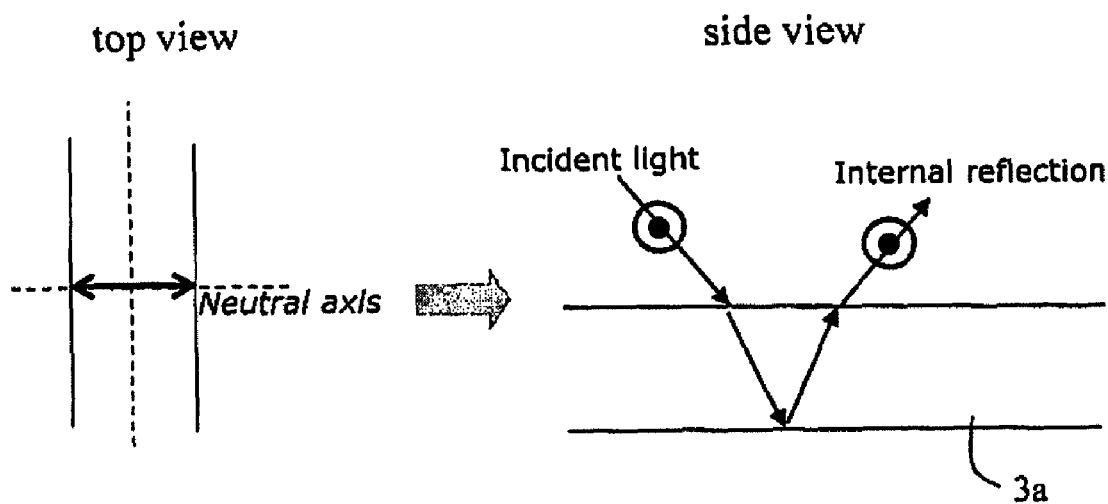
FIG. 4a schematically shows a top view and a side view of a model of internally reflected light in a single fiber for incident light of which the polarization direction is parallel to the neutral axis of the fiber.

Case i) is schematically shown in FIG. 4a. The polarization state of the light is not modified while propagating through the fiber. Thus, the internally reflected light component is completely polarized and its polarization state is preserved.

Figure 4B:
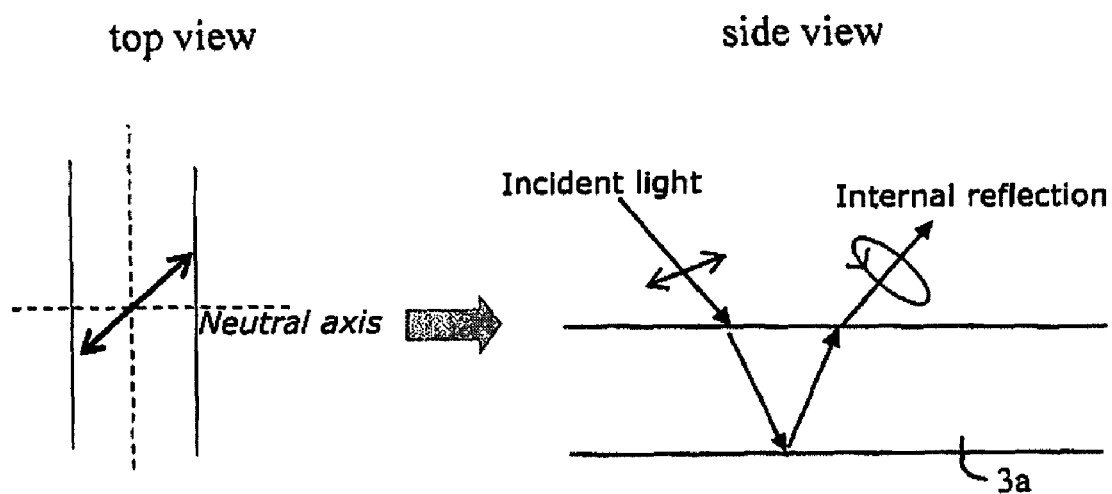
FIG. 4b schematically shows a top view and a side view of a model of internally reflected light in a single fiber for incident light of which the polarization direction is at 45° to the neutral axis of the fiber.

Case ii) is schematically shown in FIG. 4b. The different amount of birefringence experienced by the different polarization components mixed together makes it so that the light from the internal reflection is circularly polarized.

If the incident light is polarized otherwise than in cases i) and ii), the internally reflected light will be elliptically polarized.

According to the present disclosure, the orientation of randomly and regularly arranged birefringent fibers is measured using an apparatus as shown in FIG. 2. As shown in the example of FIG. 3, the light coming from the hair 3a on the mannequin head 3, containing the three components external reflection, internal reflection, and diffusion as described above, is detected by the imaging system 7. The observed light first passes through the PSA 19 before entering the objective lens 25 of the video camera 21. The intensity of the observed light measured this way depends on the state of the polarization analyzer 19. Preferably, the intensity measurement of the light coming from the mannequin head 3 is realized by taking images of the mannequin head 3 with the video camera 21 at a given video frame rate. The video camera 21 may be, for example, a color camera working in the visible spectrum. The video camera 21 is controlled by the image acquisition unit 11. The apparatus 1 according to the present disclosure may further comprise one or a plurality of filters in front of the camera 21 adapted to reject undesired wavelengths.

As an example, two cases for the polarization states of the illumination and the observation channel may be distinguished:
  (a) the PSG 17 and the PSA 19 are in the same state, i.e., the incident light and the detected light have parallel polarization, or
  (b) the PSG 17 and the PSA 19 are in crossed states, i.e., the polarization of the incident light is orthogonal to the polarization of the detected light.

In the case of parallel polarization for illumination and observation (case (a)), the intensity signal $I_{//}$ detected by the imaging system 7 may be written as:

$$I_{//} = S + \frac{D}{2} + \beta C, \quad (1)$$

wherein S, C, and D designate the external reflection component, the internal reflection component, and the diffusion component, respectively, and β is the modulation amplitude of the internal reflection component C. It is supposed that the internal reflection is due to a refraction of the incident light on the surface of a fiber followed by a single reflection on the inner surface of the fiber, and further followed by another refraction of the light exiting the fiber. Incident light polarized at 0° with respect to the neutral axis of the fiber experiences a coefficient of refraction that is lower than that for light polarized at 90°, and incident light polarized a 0° is reflected in a greater proportion than light polarized at 90°. Thus, the entrance and exit refractions favor light polarized at 90° while the internal reflection favors light polarized at 0°. If the refraction and internal reflection processes do not compensate each other exactly, the internal reflection is stronger for one of the two polarization states of the incident light.

Figure 5A:
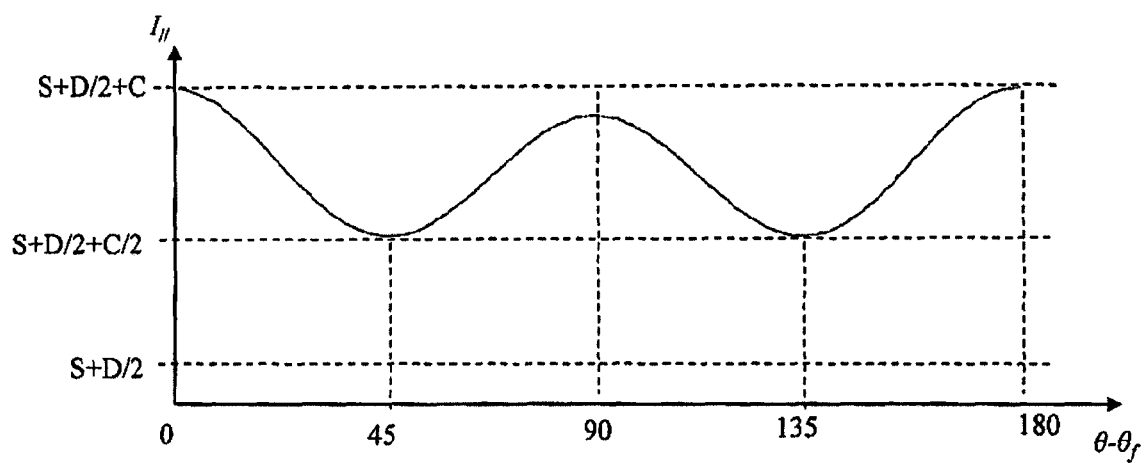
FIGS. 5a and 5b show graphs of measured intensities using the apparatus according to the present disclosure in the case of parallel polarization for illumination and observation and in the case of crossed polarizations for illumination and observation, respectively.

The internal reflection modulation amplitude can be described by the following equation:

$$\beta = \frac{3}{4} + \frac{1}{4}\cos(4(\theta - \theta_f))[1 - M\cos(2(\theta - \theta_f))], \quad (2)$$

wherein M takes into account the dependence of the internal reflection on the polarization state of the incident light, θ is the polarization angle of the incident light, and $\theta_f$ the orientation of the neutral axis of the fiber. The polarization angles θ are set with respect to 0° which is chosen arbitrarily. FIG. 5a shows the variation of $I_{//}$ versus $\theta - \theta_f$.

In the case of crossed polarizations for illumination and observation (case (b)), the intensity signal $I_\perp$ detected by the imaging system may be written as $$I_\perp = \frac{D}{2} + (1 - \beta)C, \quad (3)$$

Figure 5B:
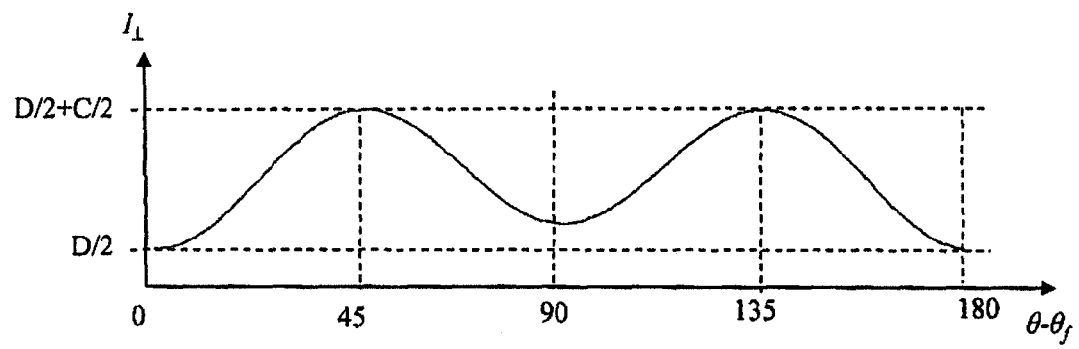

FIG. 5b shows the variation of $I_\perp$ versus $\theta - \theta_f$.

Measurements of the light modulation show that M cos(2(θ−θ_f))<<1. Therefore, the internal reflection modulation amplitude of eq. (2) can be expressed as $$\beta = \frac{3}{4} + \frac{1}{4}\cos(4(\theta - \theta_f)). \quad (4)$$

According to the present disclosure, N images are acquired corresponding to N couples of polarization states ($PSG_N$, $PSA_N$). Preferably, N≧4. A set of N equations with 4 unknowns is then analytically resolved.

We will now describe an example with N=4. Here, one image is taken in parallel configuration (parallel linear polarizations for illumination and observation, $PSG_N = PSA_N$, case (a) described above), and 3 images are taken with orthogonal configuration (crossed polarizations for illumination and observation, $PSG_N \perp PSA_N$, case (b) described above). To achieve this, 3 arbitrary orientations of the PSG (θ=0°, 30°, and 60°) and 3 different orientations of the PSA (0°, 120°, and 150°) may be chosen, wherein θ=0° is arbitrarily set. Any other couples and combinations of couples of ($PSG_N$, $PSA_N$)

may be employed, whereby the couples need to be different from each other for the N image acquisitions.

In each pixel of the 4 images, the intensities $I_1$, $I_2$, $I_3$ and $I_4$, respectively, are measured. The set of equations corresponding to each pixel of the 4 acquired images may be written as follows:

$$I_1 = S + \left(\frac{3}{4} + \frac{1}{4}\cos(4\theta_f)\right)C + \frac{D}{2} \quad (5)$$

$$I_2 = \left(1 - \frac{3}{4} - \frac{1}{4}\cos(4\theta_f)\right)C + \frac{D}{2}$$

$$I_3 = \left(1 - \frac{3}{4} - \frac{1}{4}\cos\left(4\left(\frac{\pi}{6} - \theta_f\right)\right)\right)C + \frac{D}{2}$$

$$I_4 = \left(1 - \frac{3}{4} - \frac{1}{4}\cos\left(4\left(\frac{\pi}{3} - \theta_f\right)\right)\right)C + \frac{D}{2}.$$

The analytical resolution gives the following set of solutions:

$$C = \frac{8}{3}\sqrt{I_2^2 + I_3^2 + I_4^2 - (I_2 I_3 + I_2 I_4 + I_3 I_4)} \quad (6)$$

$$D = \frac{2}{3}(I_2 + I_3 + I_4) - \frac{C}{2}$$

$$S = I_1 + I_2 - (C + D)$$

$$\theta_f = \frac{1}{4}\arctan\left(\frac{3(I_3 - I_4)}{\sqrt{3}(2I_2 - I_3 - I_4)}\right) + k\frac{\pi}{4},$$

wherein k is an integer. The angle $\theta_f$ may thus be determined modulo $\pi/4$.

Other couples of ($PSG_N$, $PSA_N$) lead to other sets of equations (5), but the same values of C, D, S, and $\theta_f$ (6) are obtained. Furthermore, the use of circularly or elliptically polarized light for the illumination and the observation will lead to similar decomposition results.

The synchronization of the elements of the apparatus is carried using a synchronization unit 31. The synchronization unit may be comprised in the control unit 9 as shown in FIG. 2, or it may be apart. The PSG 17, the PSA 19, the video camera 21, and the display may be synchronized. Preferably, the synchronization is implemented electronically.

Figure 6A:
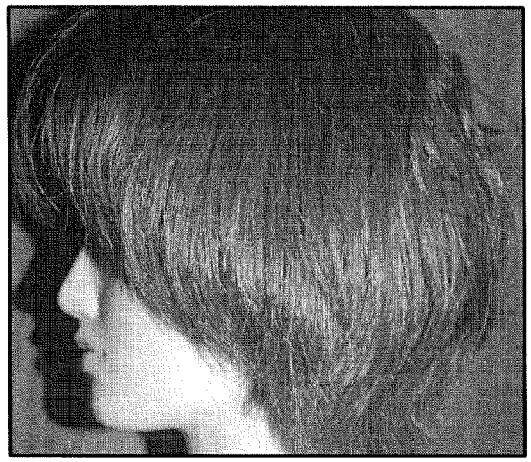
FIGS. 6a-d show examples of images of a mannequin head taken with the apparatus according to the present disclosure, where
Figure 6B:
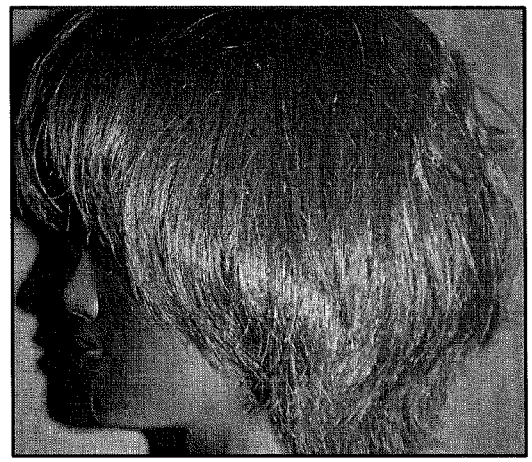
Figure 6C:
Figure 6D:

Referring now to FIGS. 6a-d, images of a mannequin head showing the separated components of light coming from the mannequin hair are shown. In FIG. 6a is an image of the total intensity measured on the mannequin head. FIGS. 6b-6d only show the external reflection component, the internal reflection component, and the diffusion component, respectively. In the case of hair fibers, the respective amounts of the three components and thus their visual appearance depend on the hair color.

Depending on the kind of light source and the characteristics thereof, different realization examples of the apparatus according to the present disclosure may be considered. For example, an apparatus using a cw laser source or LEDs may be used in the laboratory where it is possible to work in a dark environment. Further, a field system would rather employ a pulsed or flashed light source to make it more suitable for working in a normal environment presenting background light of which the acquisition needs to be minimized. The choice of a laboratory or a field system also depends on the polarizers comprised by the PSG and the PSA and their switching times.

Advantageously, apparatus and method of the present disclosure may provide at least one of the following advantages. The laboratory system is easy to implement and all the elements of the apparatus as well as the image acquisition can be controlled by the control unit, for example a personal computer. The field system allows for a very fast image acquisition and output. In either case, neither knowledge nor assumptions about the fiber orientation are needed, i.e., the fibers may be mutually randomly and/or regularly organized.

The method and apparatus according to the present disclosure may be implemented with several applications. For example, the formulation of hair care or hair styling products may be improved in order to obtain the desired visual appearance of the hair. The hair care products may be formulated so as to influence on the light interaction with the hair and thus enhance the shine of the hair, amplify or change its color, etc. Because information and images of the different light components (shine, color, and diffused light) are provided, it may be possible to simulate the hair's visual appearance in advance by adjusting the amount of each contribution. Hair care products may thus be developed, for example, after consultation of a customer jury.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method to measure visual appearance of birefringent fibers, the method comprising:
   emitting light;
   creating N polarization states of the emitted light;
   illuminating the birefringent fibers with the emitted light;
   generating internal reflection components, external reflection components, and diffusion components of the emitted light;
   observing light from the illuminated birefringent fibers;
   creating N polarization states of an observed light;
   forming N images of the observed polarized light, each image comprising a plurality of pixels;
   measuring an intensity $I_i$ in each pixel of the N images; and
   for each pixel, separating the internal reflection component, the external reflection component, and the diffusion component from the i-th image for the N images, wherein i=1, 2, . . . N and N≧4.

2. The method of claim 1, wherein the birefringent fibers comprise at least one of textile fibers and hair.

3. The method of claim 1, wherein a wavelength of the emitted light is in a near infrared range.

4. The method of claim 1, wherein a wavelength of the emitted light is in a visible range.

5. The method of claim 1, wherein at least one of the polarization states of the emitted light and at least one of the polarization states of the observed light are the same.

6. The method of claim 1, wherein at least one of the polarization states of the emitted light is different from at least one of the polarization states of the observed light.

7. The method of claim 1, wherein the separating comprises analytically resolving for each pixel an equation system for the intensities $I_i$ measured in the N images.

8. The method of claim 1, wherein the fibers are regularly arranged.

9. The method of claim 1, wherein the fibers are randomly and regularly arranged.

10. An apparatus configured to measure visual appearance birefringent fibers, comprising:
- a light source;
- a first variable polarizer configured to create N polarization states of light emitted by the light source, wherein the polarized emitted light illuminates the birefringent fibers, thereby generating internal reflection components, external reflection components, and diffusion components of the light;
- a detector arranged to observe the light from the illuminated birefringent fibers;
- a second variable polarizer configured to create N polarization states of the observed light,
- wherein the detector form N images of the observed polarized light, each image comprising a plurality of pixels; and
- an image processing unit configured to:
   - measure an intensity $I_i$ in each pixel of the N images; and
   - for each pixel, separate the internal reflection component, the external reflection component, and the diffusion component from the i-th image for the N images, wherein i=1, 2, . . . N and N≧4.

11. The apparatus of claim 10, wherein the light source comprises a pulsed laser source.

12. The apparatus of claim 10, wherein the light source comprises a continuous wave laser source.

13. The apparatus of claim 10, wherein the light source comprises at least one light emitting diode.

14. The apparatus of claim 10, wherein the light source comprises a flash lamp.

15. The apparatus of claim 10, wherein the detector comprises a video camera.

16. The apparatus of claim 10, wherein each one of the first and the second variable polarizers are one of actively and passively controlled.

17. The apparatus of claim 10, wherein the first and the second variable polarizers are incorporated in a single polarizer.

18. The apparatus of claim 10, wherein N first and second polarizers are mounted on one rotation stage.

19. The apparatus of claim 10, wherein the image processing unit and a processor are incorporated in a computer.

20. The apparatus of claim 10, further comprising a synchronization unit configured to synchronize the first and second variable polarizers and the detector.

21. The apparatus of claim 10, wherein the birefringent fibers are regularly arranged.

22. The apparatus of claim 10, wherein the birefringent fibers are randomly and regularly arranged.

* * * * *